US006498264B2

(12) United States Patent
Tonomura et al.

(10) Patent No.: US 6,498,264 B2
(45) Date of Patent: Dec. 24, 2002

(54) SILYL (METH)ACRYLATES HAVING BULKY SUBSTITUENT GROUP AND PREPARATION THEREOF

(75) Inventors: Yoichi Tonomura, Nakakubiki-gun (JP); Tohru Kubota, Nakakubiki-gun (JP); Yasufumi Kubota, Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/087,822

(22) Filed: Mar. 5, 2002

(65) Prior Publication Data

US 2002/0128503 A1 Sep. 12, 2002

(30) Foreign Application Priority Data

Mar. 6, 2001 (JP) ........................................ 2001-061293

(51) Int. Cl.$^7$ .................................................. C07F 7/18
(52) U.S. Cl. ....................................... 556/442; 556/466
(58) Field of Search .................................. 556/442, 466

(56) References Cited

U.S. PATENT DOCUMENTS

| 4,593,055 A | | 6/1986 | Gitlitz et al. ................ 523/122 |
| 4,625,043 A | * | 11/1986 | Saito ........................... 556/442 |

FOREIGN PATENT DOCUMENTS

| EP | 1 016 681 A2 | | 7/2000 |
| JP | 62-178593 | * | 8/1987 |
| JP | 5-25188 | * | 2/1993 |
| JP | 6-228163 | * | 8/1994 |
| JP | 3053081 B2 | | 6/2000 |

* cited by examiner

*Primary Examiner*—Porfirio Nazario-Gonzalez
(74) *Attorney, Agent, or Firm*—Millen, White, Zelano & Branigan, P.C.

(57) ABSTRACT

Silyl (meth)acrylate compounds each having attached to a silicon atom one very bulky tertiary hydrocarbon group and two branched hydrocarbon groups each having a hydrocarbon group at α- or β-position or two cyclic hydrocarbon groups are very stable to hydrolysis and are useful raw materials from which hydrolyzable, self-erodible polymers for ship bottom paints are prepared.

3 Claims, 10 Drawing Sheets

SILYL (METH)ACRYLATES HAVING BULKY SUBSTITUENT GROUP AND PREPARATION THEREOF

This invention relates to novel silyl (meth)acrylate compounds having a bulky substituent group and a method for preparing the same. These novel compounds are useful raw materials for hydrolyzable, self-erodible polymers for use in ship bottom paints.

BACKGROUND OF THE INVENTION

Ship bottom paints are generally based on hydrolyzable, self-erodible polymers which are usually copolymers of tributyltin methacrylate with methyl methacrylate or the like. These copolymers are hydrolyzed in water to release bis(tributyltin) oxide while the hydrolyzed polymer moiety becomes a water-soluble carboxylic acid and thus dissolved in water so that the coating always presents an active surface. However, the bis(tributyltin) oxide released upon hydrolysis of the copolymers is strongly toxic and imposes concern for water pollution and ecological damages.

There is a need for tin-free polymers. Typical tin-free polymers are disclosed in Japanese Patent No. 3,053,081 and U.S. Pat. No. 4,593,055. Trialkylsilyl (meth)acrylates such as tributylsilyl methacrylate and triisopropylsilyl acrylate are used instead of tributyltin methacrylate and copolymerized with alkyl methacrylates.

However, the trialkylsilyl (meth)acrylates described in these patents fail to give satisfactory results. Even when truisopropylsilyl acrylate which is most bulky and most stable to hydrolysis among them is used, its copolymers still have such a hydrolysis rate that the copolymers are rapidly dissolved away. Thus a demand exists for silyl (meth)acrylate compounds which are more stable to hydrolysis.

SUMMARY OF THE INVENTION

An object of the invention is to provide silyl (meth)acrylate compounds which are more stable to hydrolysis and a method for preparing the same.

The inventor has found that a silyl (meth)acrylate compound having attached to a silicon atom one very bulky tertiary hydrocarbon group and two branched hydrocarbon groups each having a hydrocarbon group at α- or β-position or two cyclic hydrocarbon groups is more stable to hydrolysis than the prior art silyl (meth)acrylate compounds.

According to the invention, there is provided a silyl (meth)acrylate compound having a bulky substituent group, represented by the following general formula (1).

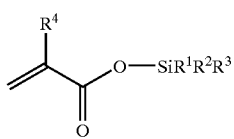

(1)

Herein $R^1$ and $R^2$ each are independently a monovalent branched hydrocarbon group having a hydrocarbon group at α- or β-position and having 3 to 10 carbon atoms or a monovalent cyclic hydrocarbon group having 3 to 10 carbon atoms, $R^3$ is a tertiary hydrocarbon group having 4 to 10 carbon atoms, and $R^4$ is hydrogen or methyl.

According to the method of the invention, the silyl (meth)acrylate compound having a bulky substituent group of the formula (1) is prepared by reacting a chlorosilane compound having the following general formula (2):

$$R^1R^2R^3SiCl \qquad (2)$$

wherein $R^1$, $R^2$ and $R^3$ are as defined above with acrylic or methacrylic acid in the presence of a basic compound.

DESCRIPTION OF THE PREFERRED EMBODIMENT

Figure 1:
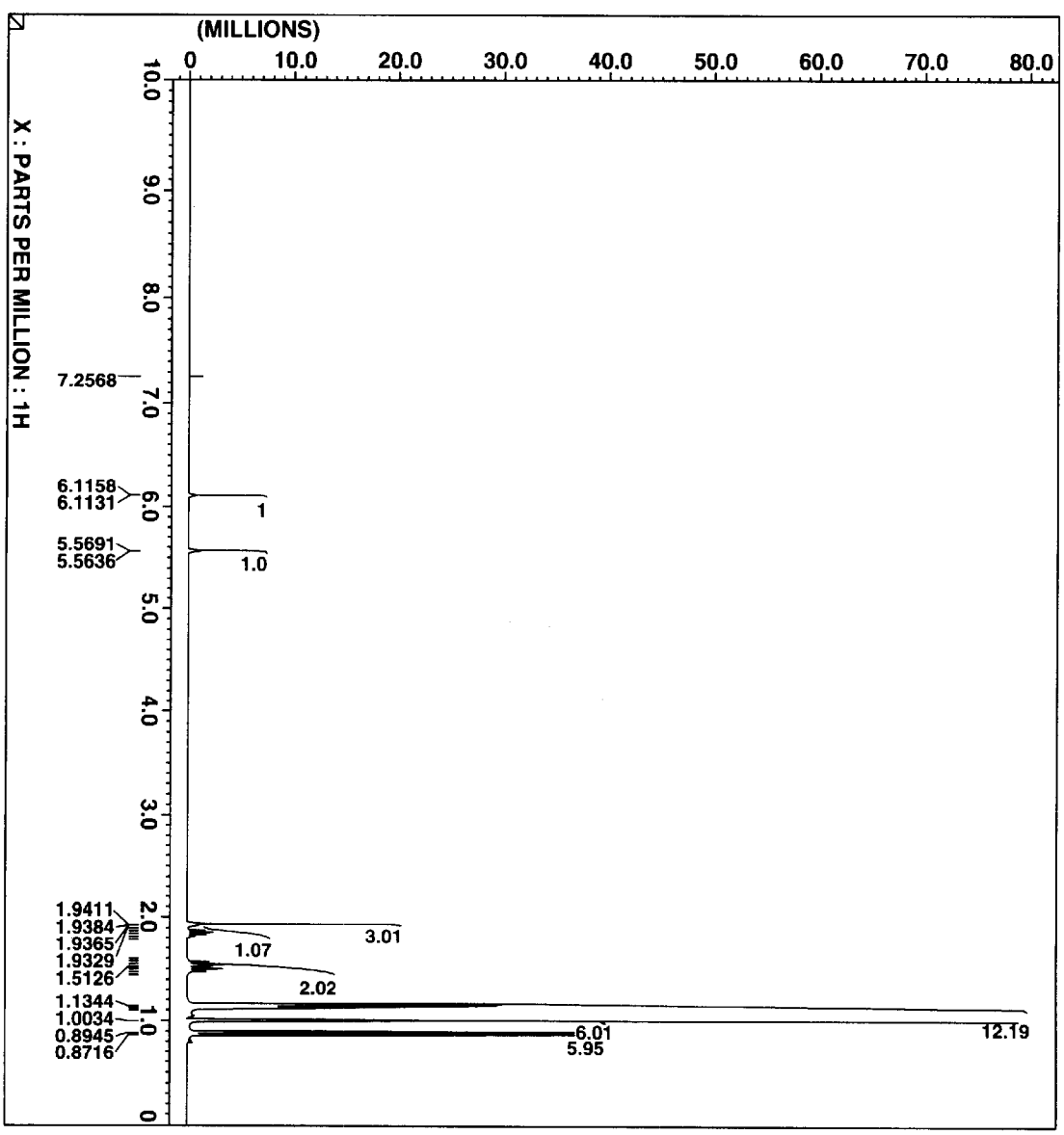
FIGS. 1 and 2 are proton-NMR and IR spectra of methacryloxythexyldiisopropylsilane synthesized in Example 1, respectively.

The silyl (meth)acrylate compound having a bulky substituent group according to the invention has the following general formula (1).

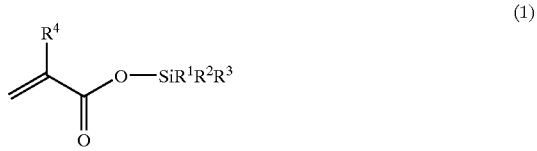

(1)

Herein each of $R^1$ and $R^2$, which may be the same or different, is a monovalent branched hydrocarbon group having a hydrocarbon group at α- or β-position and having 3 to 10 carbon atoms or a monovalent cyclic hydrocarbon group having 3 to 10 carbon atoms, $R^3$ is a tertiary hydrocarbon group having 4 to 10 carbon atoms, and $R^4$ is hydrogen or methyl.

The branched and cyclic C(3–10) hydrocarbon groups represented by $R^1$ and $R^2$ are preferably branched alkyl groups and cycloalkyl groups, for example, isopropyl, isobutyl, sec-butyl, 1-methylbutyl, 1-ethylpropyl, 2-ethylhexyl, cyclopentyl and cyclohexyl. Of these, isopropyl and isobutyl are preferred. Examples of the tertiary C(4–10) hydrocarbon group represented by $R^3$ include tert-butyl, tert-amyl, 1,1-diethylpropyl, 1,1,2-trimethylpropyl (i.e., thexyl), 1-methylcyclopentyl, and 1-methylcyclohexyl, with tert-butyl and 1,1,2-trimethylpropyl being preferred.

Illustrative, non-limiting examples of the bulky substituent group-bearing silyl (meth)acrylate of the formula (1) include methacryloxythexyldiisopropylsilane, acryloxythexyldiisopropylsilane, methacryloxythexyldiisobutylsilane, acryloxythexyldiisobutylsilane, methacryloxythexyldi-sec-butylsilane, acryloxythexyldi-sec-butylsilane, methacryloxythexyldi(1-methylbutyl)silane, acryloxythexyldi(1-methylbutyl)silane, methacryloxythexyldi(1-ethylpropyl)silane, acryloxythexyldi(1-ethylpropyl)-silane, methacryloxythexyldi(2-ethylhexyl)silane, acryloxythexyldi(2-ethylhexyl)silane, methacryloxythexyldicyclopentylsilane, acryloxythexyldicyclopentylsilane, methacryloxythexyldicyclohexylsilane, acryloxythexyldicyclohexylsilane, methacryloxythexylisopropylisobutylsilane, acryloxythexylisopropylisobutylsilane, methacryloxythexylisopropyl-sec-butylsilane, acryloxythexylisopropyl-sec-butylsilane, methacryloxy-tert-butyldiisopropylsilane, acryloxy-tert-butyldiisopropylsilane, methacryloxy-tert-butyldiisobutyl-silane, acryloxy-tert-butyldiisobutylsilane, methacryloxy-tert-butyldi-sec-butylsilane, acryloxy-tert-butyldi-sec-butylsilane, methacryloxy-tert-butyldi(1-methylbutyl)silane, acryloxy-tert-butyldi(1-methylbutyl)silane, methacryloxy-tert-butyldi(1-ethylpropyl)silane, acryloxy-tert-butyldi(1-ethylpropyl)silane, methacryloxy-tert-butyldi(2-ethylhexyl)-silane, acryloxy-tert-butyldi(2-ethylhexyl)silane, methacryloxy-tert-butyldicyclopentylsilane, acryloxy-tert-butyldicyclopentylsilane, methacryloxy-tert-butyldicyclohexylsilane, acryloxy-tert-butyldicyclohexylsilane, methacryloxy-tert-butylisopropylisobutylsilane, acryloxy-tert-butylisopropylisobutylsilane, methacryloxy-tert-butylisopropyl-sec-butylsilane, acryloxy-tert-butylisopropyl-sec-butylsilane, methacryloxy-tert-amyldiisopropylsilane, acryloxy-tert-amyldiisopropylsilane, methacryloxy-tert-amyldiisobutylsilane, acryloxy-tert-amyldiisobutyl-silane, methacryloxy-tert-amyldi-sec-butylsilane, acryloxy-tert-amyldi-sec-butylsilane, methacryloxy-tert-amyldi(1-methylbutyl)silane, acryloxy-tert-amyldi(1-methylbutyl)-silane, methacryloxy-tert-amyldi(1-ethylpropyl)silane, acryloxy-tert-amyldi(1-ethylpropyl)silane, methacryloxy-tert-amyldi(2-ethylhexyl) silane, acryloxy-tert-amyldi(2-ethylhexyl)silane, methacryloxy-tert-amyldicyclopentyl-silane, acryloxy-tert-amyldicyclopentylsilane, methacryloxy-tert-amyldicyclohexylsilane, acryloxy-tert-amyldicyclohexyl-silane, methacryloxy-tert-amylisopropylisobutylsilane, acryloxy-tert-amylisopropylisobutylsilane, methacryloxy-tert-amylisopropyl-sec-butylsilane, acryloxy-tert-amyliso-propyl-sec-butylsilane, etc.

Of these, methacryloxythexyldiisopropylsilane, acryloxythexyldiisopropylsilane, methacryloxythexyldiisobutylsilane, acryloxythexyldiisobutylsilane, methacryloxy-tert-butyldiisopropylsilane, acryloxy-tert-butyldiisopropylsilane, methacryloxy-tert-butyldiisobutylsilane, and acryloxy-tert-butyldiisobutylsilane are preferred because their products are more useful and they are easy to prepare.

The bulky substituent group-bearing silyl (meth)acrylate compound of the formula (1) according to the invention is prepared, for example, by reacting a bulky substituent group-bearing chlorosilane compound of the following general formula (2) with acrylic or methacrylic cid in the presence of a basic compound.

$R^1R^2R^3SiCl$ (2)

Herein $R^1$ and $R^2$ each are independently a monovalent branched C(3–10) hydrocarbon group having a hydrocarbon group at α- or β-position or a monovalent cyclic C(3–10) hydrocarbon group, and $R^3$ is a tertiary C(4–10) hydrocarbon group.

The branched and cyclic C(3–10) hydrocarbon groups represented by $R^1$ and $R^2$ in formula (2) are preferably branched alkyl groups and cycloalkyl groups, for example, isopropyl, isobutyl, sec-butyl, 1-methylbutyl, 1-ethylpropyl, 2-ethylhexyl, cyclopentyl and cyclohexyl. Of these, isopropyl and isobutyl are preferred. Examples of the tertiary C(4–10) hydrocarbon group represented by $R^3$ include tert-butyl, tert-amyl, 1,1-diethylpropyl, 1,1,2-trimethylpropyl (i.e., thexyl), 1-methylcyclopentyl, and 1-methylcyclohexyl, with tert-butyl and 1,1,2-trimethylpropyl being preferred.

Illustrative, non-limiting examples of the chlorosilane compound of the formula (2) include thexyldiisopropylchlorosilane, thexyldiisobutylchlorosilane, thexyldi-sec-butylchlorosilane, thexyldi(1-methylbutyl)-chlorosilane, thexyldi(1-ethylpropyl)chlorosilane, thexyldi(2-ethylhexyl) chlorosilane, thexyldicyclopentylchlorosilane, thexyldicyclohexylchlorosilane, thexylisopropylisobutylchlorosilane, thexylisopropyl-sec-butylchlorosilane, tert-butyldiisopropylchlorosilane, tert-butyldiisobutylchlorosilane, tert-butyldi-sec-butylchlorosilane, tert-butyldi(1-methylbutyl)chlorosilane, tert-butyldi(1-ethyl-propyl)chlorosilane, tert-butyldi(2-ethylhexyl)chlorosilane, tert-butyldicyclopentylchlorosilane, tert-butyldicyclohexylchlorosilane, tert-butylisopropylisobutylchlorosilane, tert-butylisopropyl-sec-butylchlorosilane, tert-amyldiisopropylchlorosilane, tert-amyldiisobutylchlorosilane, tert-amyldisec-butylchlorosilane, tert-amyldi(1-methylbutyl)chlorosilane, tert-amyldi(1-ethylpropyl)chlorosilane, tert-amyldi(2-ethylhexyl)chlorosilane, tert-amyldicyclopentylchlorosilane, tert-amyldicyclohexylchlorosilane, tert-amylisopropylisobutylchlorosilane, tert-amylisopropyl-sec-butylchlorosilane, etc.

The mixing proportion of acrylic or methacrylic acid and the chlorosilane compound of formula (2) is not critical. From the reactivity and productivity standpoints, it is preferred to use 0.5 to 2.0 mol, especially 0.8 to 1.2 mol of the chlorosilane compound per mol of acrylic or methacrylic acid.

In addition to the end product, the reaction forms hydrochloric acid which is removed using the basic compound. Examples of the basic compound used herein include amines such as triethylamine, diethylamine, tripropylamine, dipropylamine, diisopropylamine, diisopropylmethylamine, diisopropylethylamine, tributylamine, aniline, N,N-dimethylaniline and N,N-dimethylaminopyridine as well as ammonia, imidazole, pyridine, sodium hydrogen carbonate, sodium carbonate, sodium methoxide and sodium ethoxide.

The amount of the basic compound added is not critical. From the reactivity and productivity standpoints, it is preferred to use 0.5 to 2.0 mol, especially 1.0 to 1.5 mol of the basic compound per mol of acrylic or methacrylic acid. Less than 0.5 mol of the basic compound is insufficient for dehydrochlorination so that reaction may proceed to a short extent whereas more than 2.0 mol of the basic compound may not achieve an additional reaction promoting effect for that increment.

The reaction temperature is preferably −20° C. to 200° C., especially 0° C. to 150° C., under atmospheric pressure or sufficient pressure, though not limited thereto.

It is noted that the reaction may take place in a solventless system. However, since the hydrochloric acid salt resulting from dehydrochlorination obstructs agitation, use of a solvent is recommended. Examples of the solvent used herein include hydrocarbon solvents such as pentane, hexane, cyclohexane, isooctane, benzene, toluene and xylene, ether solvents such as diethyl ether, tetrahydrofuran and dioxane, ester solvents such as ethyl acetate and butyl acetate, aprotic polar solvents such as acetonitrile, dimethylsulfoxide, N,N-dimethylformamide, N-methylpyrolidone and hexamethylphosphoric triamide, and chlorinated hydrocarbon solvents such as dichloromethane and chloroform. These solvents may be used alone or in admixture of any.

The reaction may be carried out in various ways, for example, by adding the chlorosilane to a liquid mixture of the basic compound, acrylic or methacrylic acid and the solvent, by adding acrylic or methacrylic acid to a liquid mixture of the basic compound, chlorosilane and solvent, or by adding both acrylic or methacrylic acid and the chlorosilane to a liquid mixture of the basic compound and solvent.

To the reaction system, a polymerization inhibitor such as hydroquinone, p-methoxyphenol, 2,6-di-tert-butylphenol or 2,6-di-tert-butyl-4-methylphenol may be added for inhibiting polymerization.

At the end of reaction, there is formed the hydrochloric acid salt of the basic compound, which can be removed by filtration of the reaction solution. After the salt removal, the end product can be recovered from the reaction solution in a conventional manner.

The bulky substituent group-bearing chlorosilane compound of formula (2) can be prepared, for example, by reacting a branched alkenyl compound having 6 to 10 carbon atoms of the following general formula (3) such as 2,3-dimethyl-2-butene with a hydrogenchlorosilane compound of the following general formula (4) in the presence of an aluminum chloride catalyst.

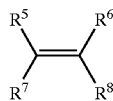
(3)

Herein, $R^5$, $R^6$, $R^7$ and $R^8$, which may be the same or different, are hydrocarbon groups having 1 to 5 carbon atoms, any two of $R^5$ to $R^8$ may form a ring, and the total number of carbon atoms in $R^5$ to $R^8$ is 6 to 10.

$$HSiR^1R^2Cl \qquad (4)$$

Herein, $R^1$ and $R^2$ are as defined above.

Illustrative, non-limiting examples of the hydrogenchlorosilane of formula (4) include diisopropylchlorosilane, diisobutylchlorosilane, di-sec-butylchlorosilane, di(1-methylbutyl)chlorosilane, di(1-ethylpropyl)chlorosilane, di(2-ethylhexyl)chlorosilane, dicyclopentylchlorosilane, dicyclohexylchlorosilane, isopropylisobutylchlorosilane, and isopropyl-sec-butylchlorosilane.

The mixing proportion of the branched alkenyl compound of formula (3) and the hydrogenchlorosilane of formula (4) is not critical although it is preferred from the reactivity and productivity standpoints to use 0.5 to 2.0 mol, especially 0.8 to 1.2 mol of the hydrogenchlorosilane per mol of the branched alkenyl compound.

The amount of aluminum chloride used as a catalyst in the above reaction is not critical. It is preferred from the reactivity and productivity standpoints to use 0.001 to 0.5 mol, especially 0.01 to 0.2 mol of the aluminum chloride per mol of the branched alkenyl compound such as 2,3-dimethyl-2-butene. Less than 0.001 mol of the catalyst may fail to provide catalysis whereas more than 0.5 mol of the catalyst may not achieve an additional reaction promoting effect for that increment.

The reaction temperature is preferably −20° C. to 150° C., especially 0° C. to 100° C., under atmospheric pressure or sufficient pressure, though not limited thereto.

Although the reaction takes place in a solventless system, a solvent is optionally used. Examples of the solvent used herein include aliphatic hydrocarbon solvents such as pentane, hexane, isooctane and cyclohexane, aprotic polar solvents such as acetonitrile, and chlorinated hydrocarbon solvents such as dichloromethane and chloroform.

The reaction may be carried out in various ways, for example, by adding aluminum chloride to a liquid mixture of the branched alkenyl compound and hydrogenchlorosilane, by adding the hydrogenchlorosilane to a liquid mixture of the branched alkenyl compound and aluminum chloride, by adding the branched alkenyl compound to a liquid mixture of the hydrogenchlorosilane and aluminum chloride, or by adding both the branched alkenyl compound and hydrogenchlorosilane to a liquid mixture of aluminum chloride and a solvent. At the end of reaction, the end product can be recovered from the reaction solution in a conventional manner.

Alternatively, the bulky substituent group-bearing chlorosilane compound of formula (2) is prepared, for example, by reacting a Grignard reagent of the following general formula (5):

$$R^3MgX^1 \qquad (5)$$

wherein $R^3$ is as defined above and $X^1$ is a halogen atom with a compound of the following general formula (6):

$$HR^1R^2SiX^2 \qquad (6)$$

wherein $R^1$ and $R^2$ are as defined above, and $X^2$ is a halogen atom and may be identical with or different from $X^1$, in the presence of a copper compound, to form a bulky substituent group-bearing hydrogensilane compound of the following general formula (7):

$$R^1R^2R^3SiH \qquad (7)$$

wherein $R^1$, $R^2$ and $R^3$ are as defined above, and chlorinating the hydrogen atom on the hydrogensilane compound.

In this procedure, the Grignard reagent of the formula (5) is used:

$$R^3MgX^1 \qquad (5)$$

wherein $R^3$ is a monovalent tertiary hydrocarbon group having 4 to 10 carbon atoms as defined above and $X^1$ is a halogen atom such as Cl or Br. Examples of the Grignard reagent include tert-butylmagnesium chloride, tert-butylmagnesium bromide, tert-amylmagnesium chloride, tert-amylmagnesium bromide, 1,1-diethylpropylmagnesium chloride, 1-methylcyclopentylmagnesium chloride and 1-methylcyclohexylmagnesium chloride.

Examples of the silane compound of formula (6) used in this procedure include diisopropylchlorosilane, diisobutylchlorosilane, di-sec-butylchlorosilane, di(1-methylbutyl)chlorosilane, di(1-ethylpropyl)chlorosilane, di(2-ethylhexyl)chlorosilane, dicyclopentylchlorosilane, dicyclohexylchlorosilane, isopropylisobutylchlorosilane, and isopropyl-sec-butylchlorosilane. On use, the silane compound of formula (6) may be in either a pure form or a crude form, that is, the reaction solution in which the compound is prepared may be used without purification.

The mixing proportion of the Grignard reagent of formula (5) and the silane of formula (6) is not critical although it is preferred from the reactivity and productivity standpoints to use 0.5 to 2.0 mol, especially 0.8 to 1.5 mol of the Grignard reagent (5) per mol of the silane (6).

The copper compound is used as a catalyst in the above reaction. Exemplary are copper (I) chloride, copper (II)

chloride, copper (I) bromide, copper (II) bromide, copper (I) iodide and copper (I) cyanide.

The amount of the copper compound used is not critical. It is preferred from the reactivity and productivity standpoints to use 0.001 to 0.1 mol. especially 0.01 to 0.05 mol of the copper compound per mol of the Grignard reagent (5). Less than 0.001 mol of the catalyst may fail to provide catalysis whereas more than 0.1 mol of the catalyst may not achieve an additional reaction promoting effect for that increment.

It is recommended to carry out the above reaction in Ian aprotic organic solvent. Useful solvents include ether solvents such as diethyl ether and tetrahydrofuran and hydrocarbon solvents such as pentane, hexane, isooctane, cyclohexane, benzene, toluene and xylene. The solvents may be used alone or in admixture of any.

The reaction temperature is preferably 0° C. to 150° C., especially 10° C. to 100° C., under atmospheric pressure or sufficient pressure, though not limited thereto. Preferably, the reaction is carried out in an inert gas atmosphere such as nitrogen or argon. If oxygen is present in the reaction system, the Grignard reagent can react with oxygen, resulting in low yields.

In the subsequent step, the hydrogensilane of formula (7) is subjected to chlorination reaction using a chlorinating agent. Suitable chlorinating agents include chlorine, thionyl chloride, allyl chloride-palladium catalyst, and methallyl chloride-palladium catalyst, with the methallyl chloride-palladium catalyst being preferred. The amount of methallyl chloride used in the chlorination reaction is not critical although it is preferred to use 0.5 to 2.0 mol of methallyl chloride per mol of the silane of formula (7).

Examples of the palladium catalyst used herein include palladium salts such as palladium chloride and palladium acetate, palladium complexes such as dichlorobistriphenylphosphine palladium, and palladium on carbon. The amount of the palladium catalyst used in the chlorination reaction is not critical although it is preferred to use 0.0001 to 0.05 mol of the palladium catalyst per mol of the silane of formula (7).

EXAMPLE

Examples of the invention are given below for further illustrating the invention, but the invention is not limited thereto.

Example 1

Methacryloxythexyldiisopropylsilane

A flask equipped with a stirrer, reflux condenser, dropping funnel and thermometer was charged with 17.2 g (0.2 mol) of methacrylic acid, 120 ml of toluene, and 0.06 g of 2,6-di-tert-butyl-4-methylphenol. At room temperature, 22.3 g (0.22 mol) of triethylamine was added dropwise over one hour. At the end of dropwise addition, the flask was heated at 80° C. After the internal temperature became constant, 47.0 g (0.20 mol) of thexyldiisopropylchlorosilane was added dropwise over two hours. After the completion of dropwise addition, the reaction solution was stirred for 5 hours at 80° C. The reaction solution was then cooled to room temperature, and the resulting hydrochloric acid salt removed by filtration. The filtrate was distilled, collecting 43.2 g of a fraction having a boiling point of 92–97° C./0.13 kPa.

Figure 2:
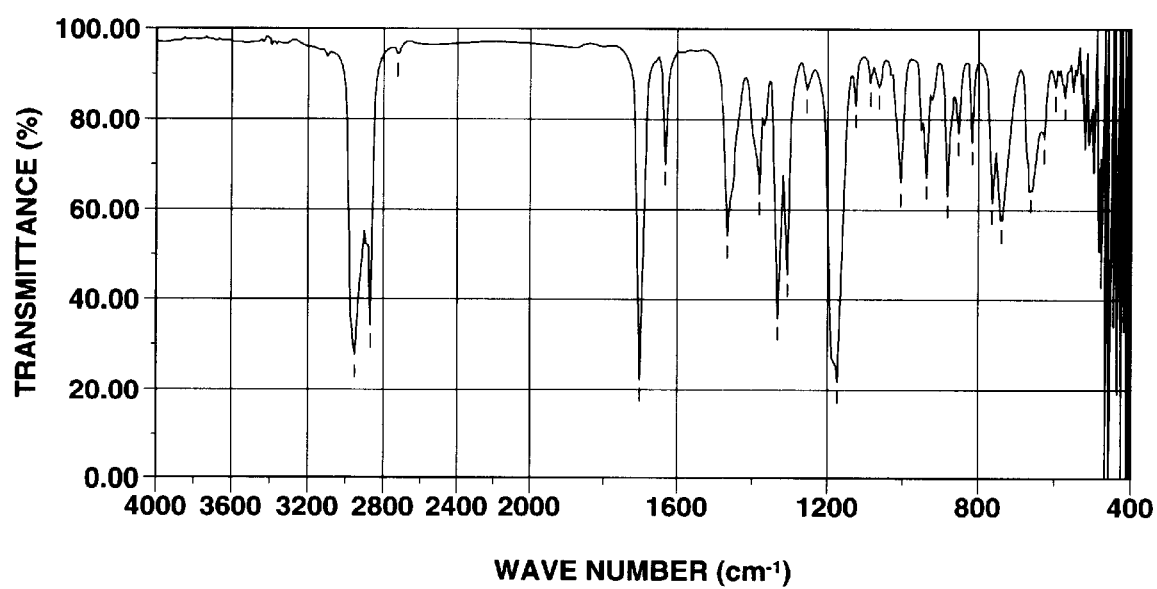

This fraction was analyzed by mass spectroscopy, $^1$H-NMR and IR spectroscopy. Mass spectrum m/z 241, 199, 69, 41; $^1$H-NMR spectrum (heavy chloroform solvent) FIG. 1; IR spectrum FIG. 2.

From these results, the compound obtained was identified to be methacryloxythexyldiisopropylsilane.

Example 2

Acryloxythexyldiisopropylsilane

A flask equipped with a stirrer, reflux condenser, dropping funnel and thermometer was charged with 14.4 g (0.2 mol) of acrylic acid, 120 ml of toluene, and 0.06 g of 2,6-di-tert-butyl-4-methylphenol. At room temperature, 22.3 g (0.22 mol) of triethylamine was added dropwise over one hour. At the end of dropwise addition, the flask was heated at 80° C. After the internal temperature became constant, 47.0 g (0.20 mol) of thexyldiisopropylchlorosilane was added dropwise over two hours. After the completion of dropwise addition, the reaction solution was stirred for 5 hours at 80° C. The reaction solution was then cooled to room temperature, and the resulting hydrochloric acid salt removed by filtration. The filtrate was distilled, collecting 38.6 g of a fraction having a boiling point of 87–92° C./0.13 kPa.

Figure 3:
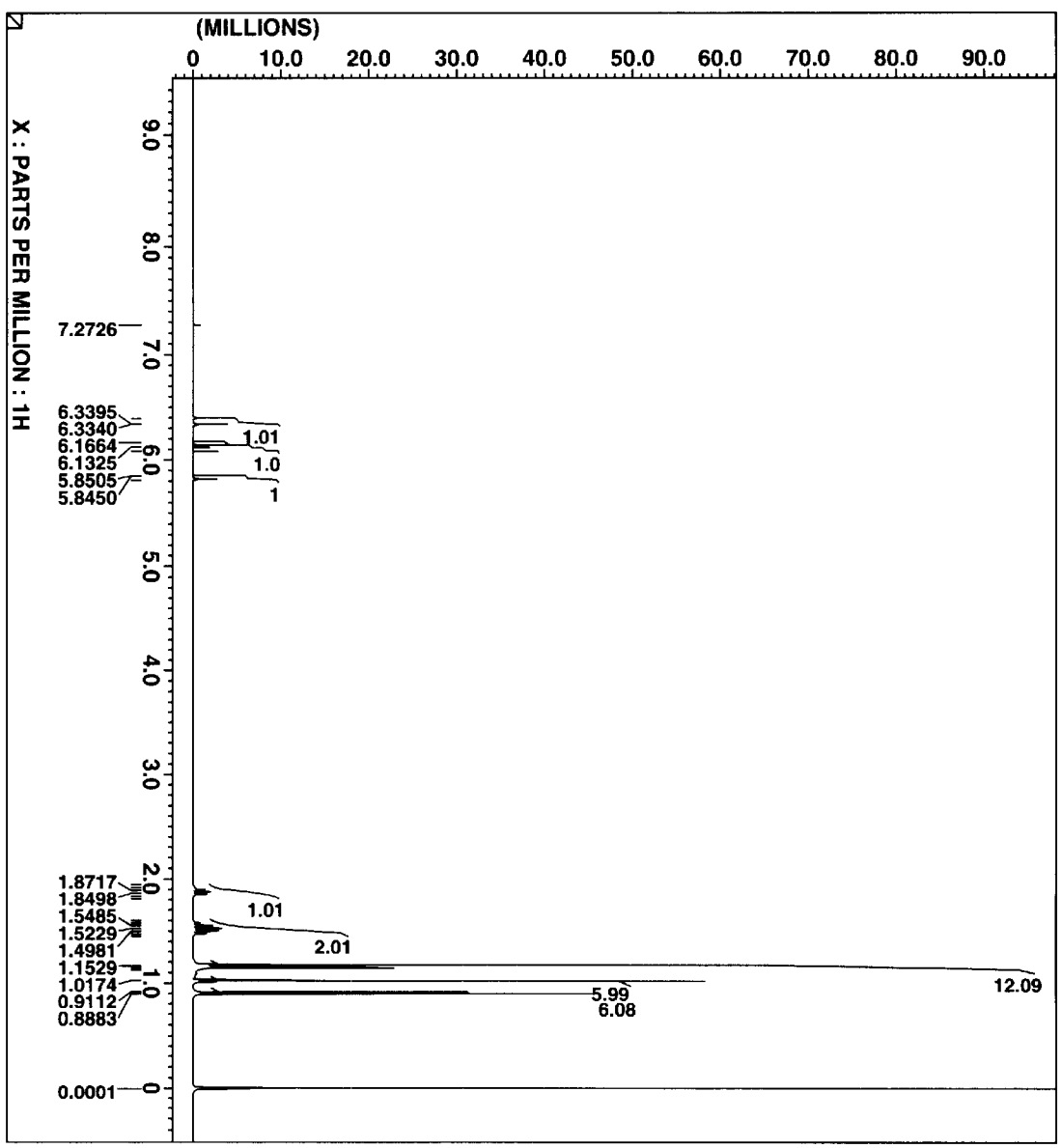
FIGS. 3 and 4 are proton-NMR and IR spectra of acryloxythexyldiisopropylsilane synthesized in Example 2, respectively.
Figure 4:
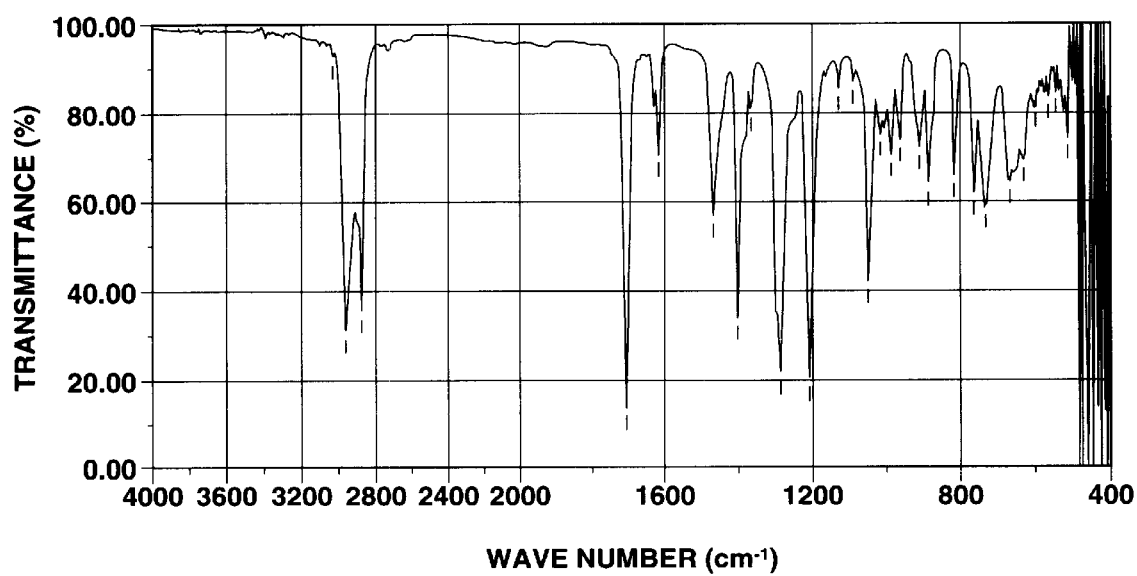

This fraction was analyzed by mass spectroscopy, $^1$H-NMR and IR spectroscopy. Mass spectrum m/z 227, 185, 55; $^1$H-NMR spectrum (heavy chloroform solvent) FIG. 3; IR spectrum FIG. 4.

From these results, the compound obtained was identified to be acryloxythexyldiisopropylsilane.

Example 3

Methacryloxythexyldiisobutylsilane

A flask equipped with a stirrer, reflux condenser, dropping funnel and thermometer was charged with 17.2 g (0.2 mol) of methacrylic acid, 120 ml of toluene, and 0.06 g of 2,6-di-tert-butyl-4-methylphenol. At room temperature, 22.3 g (0.22 mol) of triethylamine was added dropwise over one hour. At the end of dropwise addition, the flask was heated at 80° C. After the internal temperature became constant, 52.6 g (0.20 mol) of thexyldiisobutylchlorosilane was added dropwise over two hours. After the completion of dropwise addition, the reaction solution was stirred for 5 hours at 80° C. The reaction solution was then cooled to room temperature, and the resulting hydrochloric acid salt removed by filtration. The filtrate was distilled, collecting 46.3 g of a fraction having a boiling point of 104–110° C./0.13 kPa.

Figure 5:
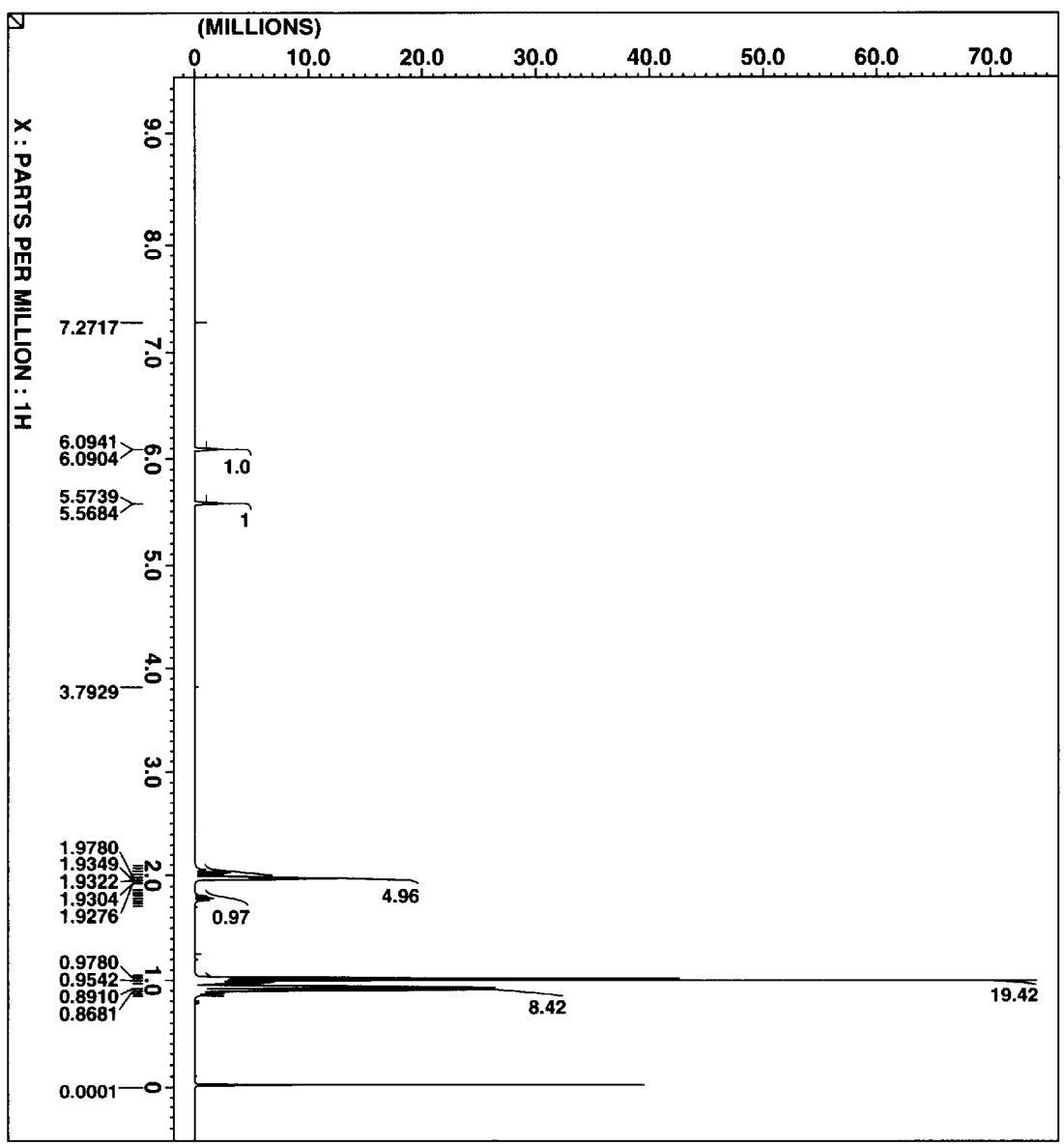
FIGS. 5 and 6 are proton-NMR and IR spectra of methacryloxythexyldiisobutylsilane synthesized in Example 3, respectively.
Figure 6:
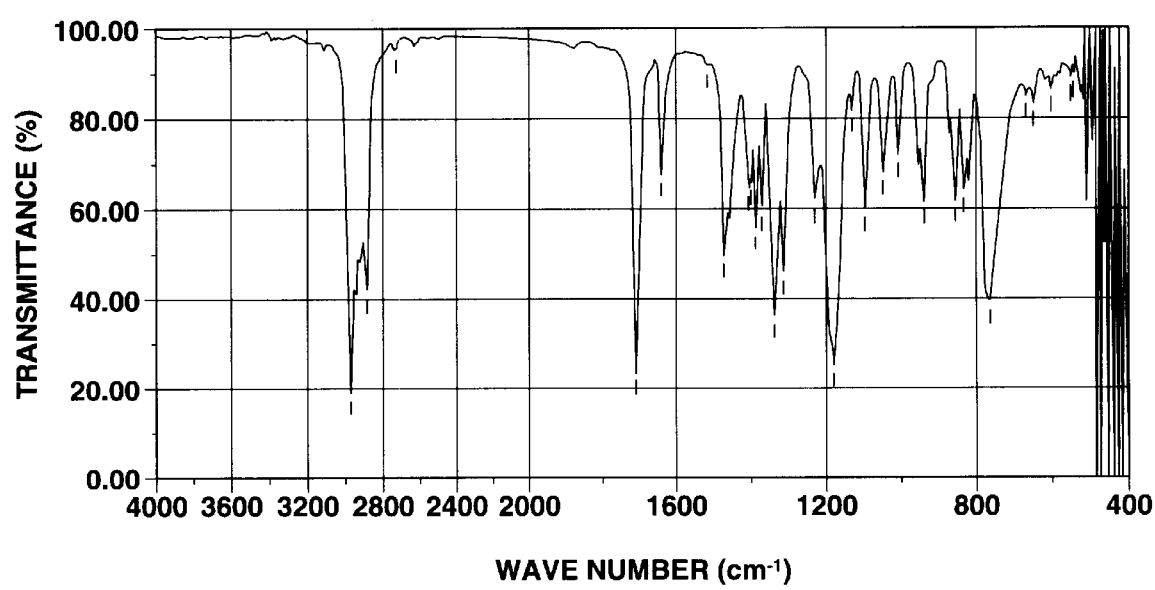

This fraction was analyzed by mass spectroscopy, $^1$H-NMR and IR spectroscopy. Mass spectrum m/z 255, 227, 69, 41; $^1$H-NMR spectrum (heavy chloroform solvent) FIG. 5; IR spectrum FIG. 6.

From these results, the compound obtained was identified to be methacryloxythexyldiisobutylsilane.

Example 4

Methacryloxy-tert-butyldiisopropylsilane

A flask equipped with a stirrer, reflux condenser, dropping funnel and thermometer was charged with 41.4 g (0.20 mol) of tert-butyldiisopropylchlorosilane, 60 ml of toluene, and 0.06 g of 2,6-di-tert-butyl-4-methylphenol. At room temperature, 22.3 g (0.22 mol) of triethylamine was added dropwise over one hour. At the end of dropwise addition, the flask was heated at 80° C. After the internal temperature became constant, 18.9 g (0.22 mol) of methacrylic acid was added dropwise over one hour. After the completion of dropwise addition, the reaction solution was stirred for 2 hours at 80° C. The reaction solution was then cooled to room temperature, and the resulting hydrochloric acid salt removed by filtration. The filtrate was distilled, collecting 45.4 g of a fraction having a boiling point of 93–95° C./0.27 kPa.

Figure 7:
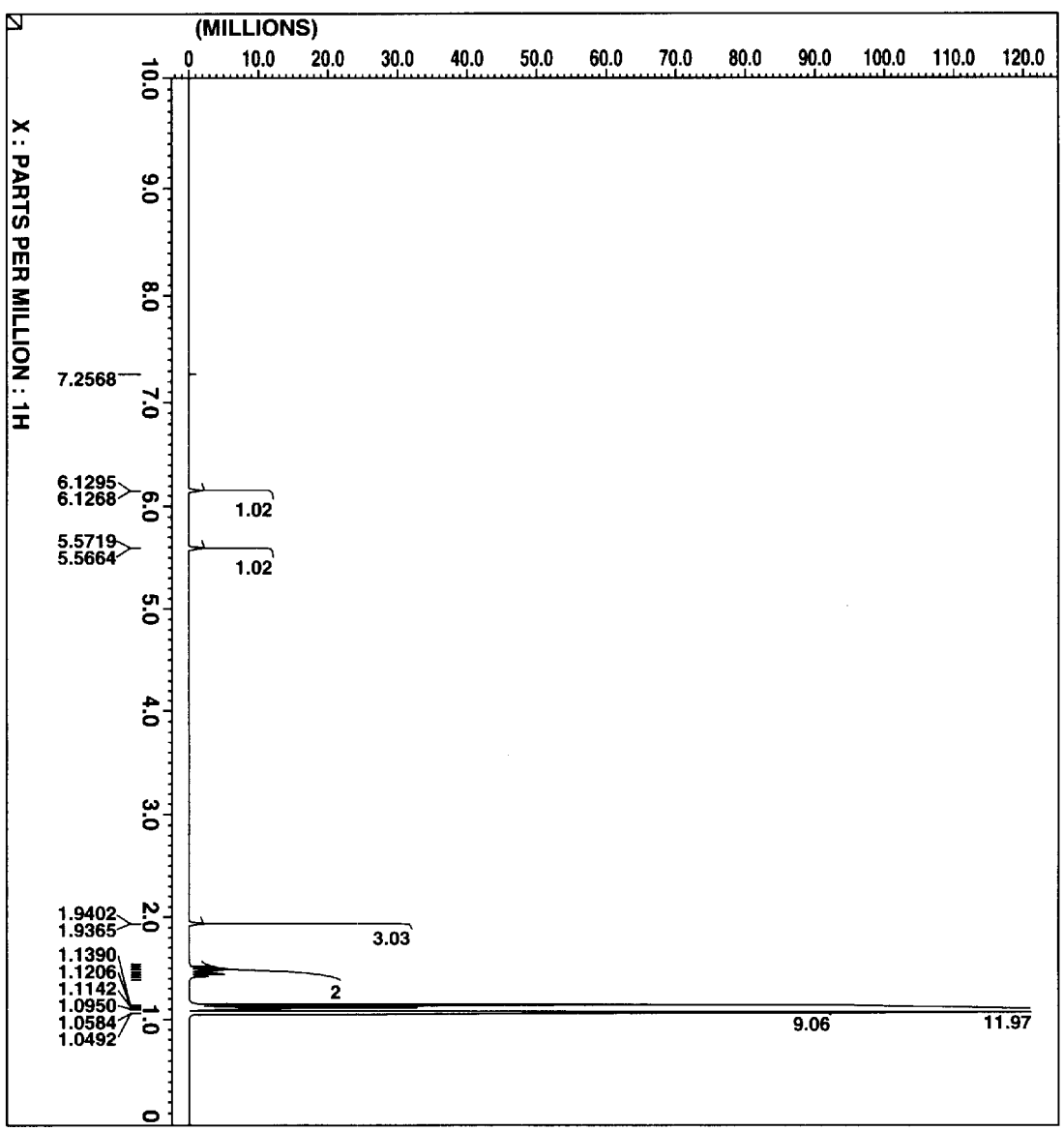
FIGS. 7 and 8 are proton-NMR and IR spectra of methacryloxy-tert-butyldiisopropylsilane synthesized in Example 4, respectively.
Figure 8:
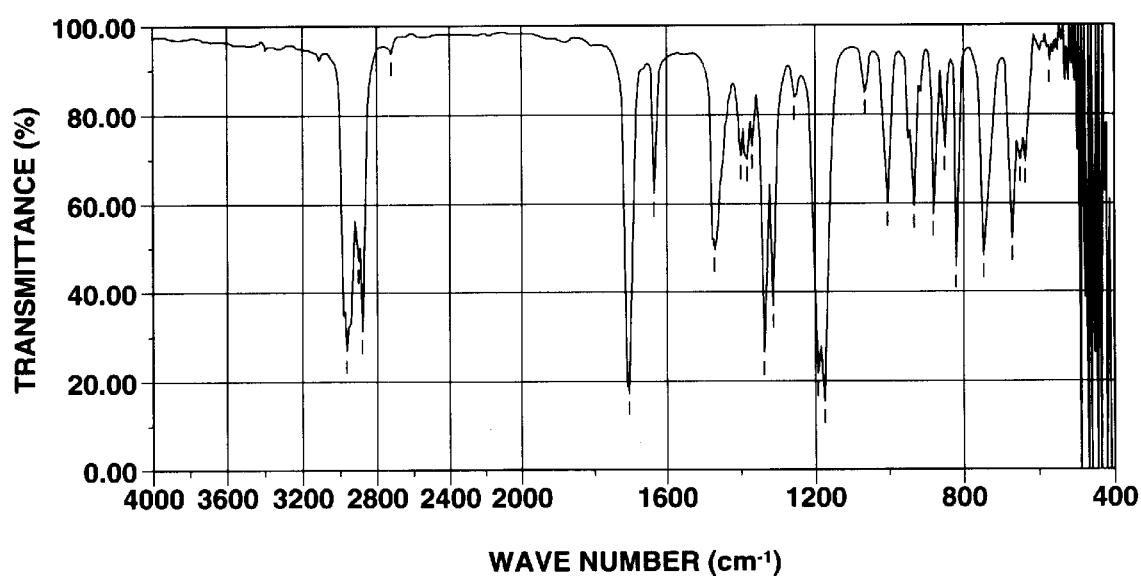

This fraction was analyzed by mass spectroscopy, $^1$H-NMR and IR spectroscopy. Mass spectrum m/z 213, 199, 69, 41; $^1$H-NMR spectrum (heavy chloroform solvent) FIG. 7; IR spectrum FIG. 8.

From these results, the compound obtained was identified to be methacryloxy-tert-butyldiisopropylsilane.

Example 5

Acryloxy-tert-butyldiisopropylsilane

A flask equipped with a stirrer, reflux condenser, dropping funnel and thermometer was charged with 41.4 g (0.20 mol) of tert-butyldiisopropylchlorosilane, 60 ml of By toluene, and 0.06 g of 2,6-di-tert-butyl-4-methylphenol. At room temperature, 22.3 g (0.22 mol) of triethylamine was added dropwise over one hour. At the end of dropwise addition, the flask was heated at 80° C. After the internal temperature became constant, 15.9 g (0.22 mol) of acrylic acid was added dropwise over one hour. After the completion of dropwise addition, the reaction solution was stirred for 2 hours at 80° C. The reaction solution was then cooled to room temperature, and the resulting hydrochloric acid salt removed by filtration. The filtrate was distilled, collecting 42.9 g of a fraction having a boiling point of 80–83° C./0.27 kPa.

Figure 9:
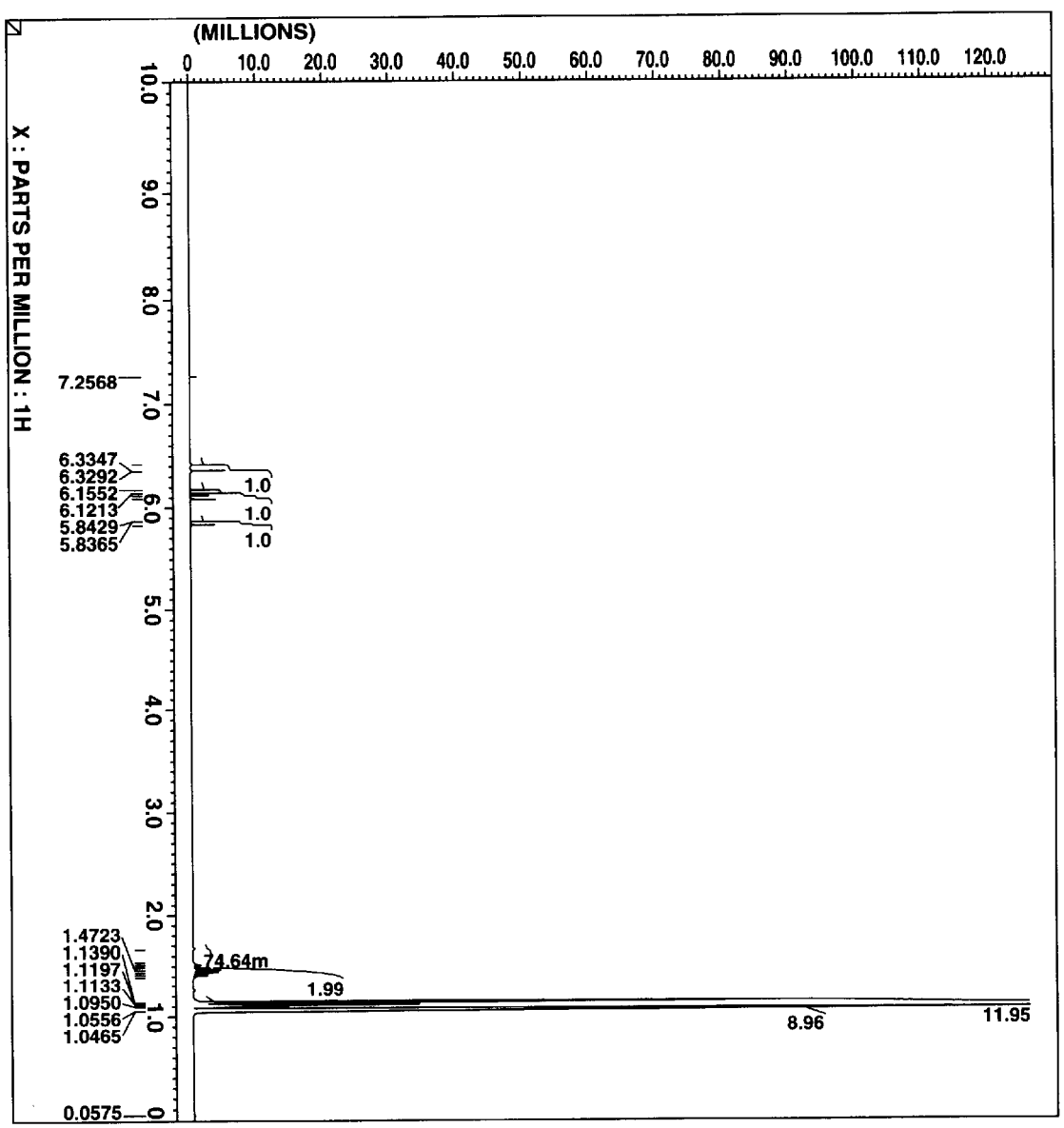
FIGS. 9 and 10 are proton-NMR and IR spectra of acryloxy-tert-butyldiisopropylsilane synthesized in Example 5, respectively.
Figure 10:
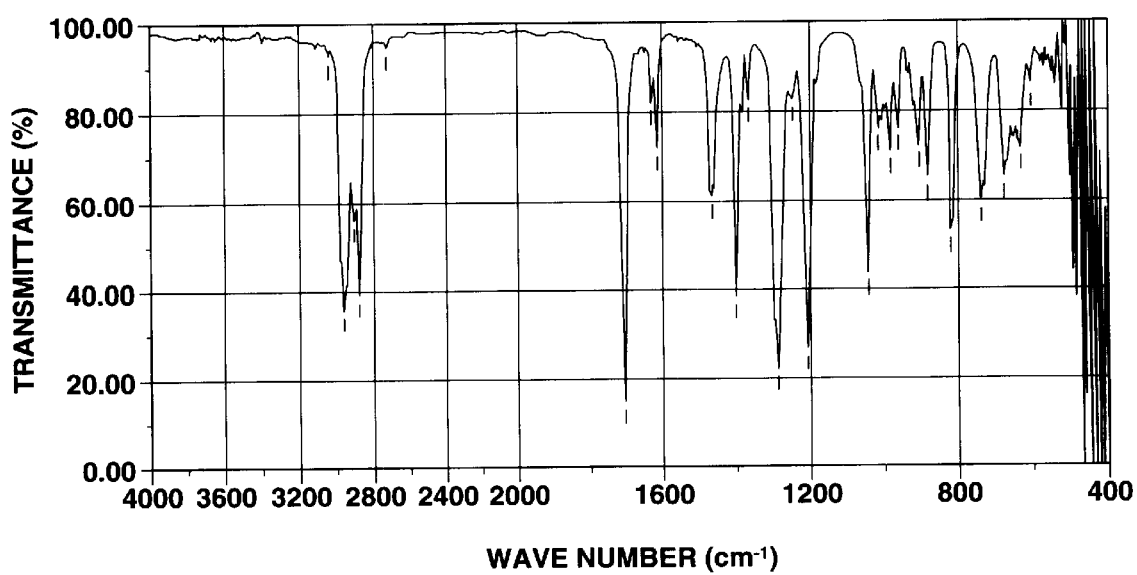

This fraction was analyzed by mass spectroscopy, $^1$H-NMR and IR spectroscopy. Mass spectrum m/z 199, 185, 55; $^1$H-NMR spectrum (heavy chloroform solvent) FIG. 9; IR spectrum FIG. 10.

From these results, the compound obtained was identified to be acryloxy-tert-butyldiisopropylsilane.

Experiment 1:

Comparison of Hydrolysis Between Methacryloxythexyldiisopropylsilane and Methacryloxytriisopropylsilane A flask equipped with a stirrer, reflux condenser and thermometer was charged with 20 g of an aqueous solution of i1% hydrogen chloride and 95% ethanol, 1.0 g of methacryloxythexyldiisopropylsilane, 1.0 g of methacryloxytriisopropylsilane and 0.5 g of xylene as an internal standard, which were stirred at room temperature. After 30 minutes of stirring, the reaction solution was analyzed by gas chromatography to find that the methacryloxythexyldiisopropylsilane was not hydrolyzed at all while the methacryloxytriisopropylsilane was entirely hydrolyzed into triisopropylsilanol.

Experiment 2:

Comparison of Hydrolysis Between Methacryloxythexyldiisobutylsilane and Methacryloxytriisopropylsilane A flask equipped with a stirrer, reflux condenser and thermometer was charged with 20 g of an aqueous solution of 1% hydrogen chloride and 95% ethanol, 1.0 g of methacryloxythexyldiisobutylsilane, 1.0 g of methacryloxytriisopropylsilane and 0.5 g of xylene as an internal standard, which were stirred at room temperature. After 30 minutes of stirring, the reaction solution was analyzed by gas chromatography to find that only 2% of the methacryloxythexyldiisobutylsilane was hydrolyzed while the methacryloxytriisopropylsilane was entirely hydrolyzed into triisopropylsilanol.

Reference Example 1

Thexyldiisopropylchlorosilane

A flask equipped with a stirrer, reflux condenser, dropping funnel and thermometer was charged with 30.1 g (0.2 mol) of diisopropylchlorosilane and 2.7 g (0.02 mol) of aluminum chloride, which were heated at 50° C. After the internal temperature became constant, 16.8 g (0.2 mol) of 2,3-dimethyl-2-butene was added dropwise over one hour. After the completion of dropwise addition, the reaction solution was stirred for one hour at 50° C. Anisole, 4.3 g (0.04 mol), was added for deactivating the aluminum chloride. The reaction solution was distilled, collecting 28.3 g of a fraction having a boiling point of 79° C./0.13 kPa.

This fraction was analyzed by mass spectroscopy, $^1$H-NMR and IR spectroscopy. Mass spectrum m/z 234 (M$^+$), 149, 121, 93, 84, 43.

From these results, the compound obtained was identified to be thexyldiisopropylchlorosilane (yield 60%).

Reference Example 2

Thexyldiisobutylchlorosilane

A flask equipped with a stirrer, reflux condenser, dropping funnel and thermometer was charged with 35.8 g (0.20 mol) of diisobutylchlorosilane and 2.7 g (0.02 mol) of aluminum chloride, which were heated at 50° C. After the internal temperature became constant, 16.8 g (0.2 mol) of 2,3-dimethyl-2-butene was added dropwise over one hour. After the completion of dropwise addition, the reaction solution was stirred for two hours at 50° C. Anisole, 4.3 g (0.04 mol), was added for deactivating the aluminum chloride. The reaction solution was distilled, collecting 32.5 g of a fraction having a boiling point of 83° C./0.13 kPa.

This fraction was analyzed by mass spectroscopy, $^1$H-NMR and IR spectroscopy. Mass spectrum m/z 262 (M$^+$), 177, 135, 95, 84, 43.

From these results, the compound obtained was identified to be thexyldiisobutylchlorosilane (yield 62%).

Reference Example 3

Tert-butyldiisopropylchlorosilane

A flask equipped with a stirrer, reflux condenser, dropping funnel and thermometer was charged with 24.3 g (1.0 mol) of metallic magnesium and 300 ml of tetrahydrofuran. In a nitrogen atmosphere, 92.6 g (1.0 mol) of tert-butyl chloride was added dropwise over one hour at an internal temperature of 40–50° C. This was stirred for one hour at 60° C., obtaining a tert-butylmagnesium chloride solution as a Grignard reagent.

To the Grignard reagent was added 1.4 g (0.01 mol) of copper bromide. At room temperature, 150.7 g (1.0 mol) of diisopropylchlorosilane was added over one hour, followed by 6 hours of stirring at 70° C. The reaction solution thus obtained was analyzed by gas chromatography to find a conversion rate of 86%. To the reaction solution, 250 g of 5% hydrochloric acid was added for dissolving the salt. The organic layer was separated and distilled, collecting 105.2 g of a fraction having a boiling point of 79° C./2.7 kPa.

This fraction was analyzed by mass spectroscopy, $^1$H-NMR and IR spectroscopy. Mass spectrum m/z 172 (M+), 115, 87, 73, 59.

From these results, the compound obtained was identified to be tert-butyldiisopropylsilane (yield 61%).

Next, a flask equipped with a stirrer, reflux condenser, dropping funnel and thermometer was charged with 45.3 g (0.5 mol) of methallyl chloride and 0.56 g (0.0025 mol) of palladium acetate, which were heated at 70° C. After the internal temperature became constant, 86.2 g (0.5 mol) of tert-butyldiisopropylsilane, obtained above, was added dropwise over 2 hours. After the completion of dropwise addition, the reaction solution was stirred for 3 hours at 100° C. The reaction solution was distilled, collecting 90.4 g (yield 87%) of a fraction having a boiling point of 81oC/1.3 kPa which was tert-butyldiisopropylchlorosilane.

There have been described bulky substituent group-bearing silyl (meth)acrylates which undergo hydrolysis at a very slow rate so that they are useful raw materials from which hydrolyzable, self-erodible polymers for ship bottom paints or the like are prepared.

Japanese Patent Application No. 2001-061293 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A silyl (meth)acrylate compound having a bulky substituent group, represented by the following general formula (1):

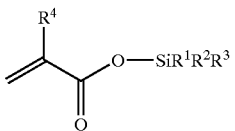

(1)

wherein $R^1$ and $R^2$ each are independently a monovalent branched hydrocarbon group having a hydrocarbon group at α- or β-position and having 3 to 10 carbon atoms or a monovalent cyclic hydrocarbon group having 3 to 10 carbon atoms, $R^3$ is a tertiary hydrocarbon group having 4 to 10 carbon atoms, and $R^4$ is hydrogen or methyl.

2. The silyl (meth)acrylate compound of claim 1 which is selected from the group consisting of methacryloxythexyldiisopropylsilane, acryloxythexyldiisopropylsilane, methacryloxythexyldiisobutylsilane, acryloxythexyldiisobutylsilane, methacryloxy-tert-butyldiisopropylsilane, acryloxy-tert-butyldiisopropylsilane, methacryloxy-tert-butyldiisobutylsilane, and acryloxy-tert-butyldiisobutylsilane.

3. A method for preparing a silyl (meth)acrylate compound having a bulky substituent group, represented by the formula (1) according to claim 1, comprising the step of reacting a chlorosilane compound with acrylic or methacrylic acid in the presence of a basic compound, the chlorosilane compound having the following general formula (2):

$$R^1R^2R^3SiCl \qquad (2)$$

wherein $R^1$ and $R^2$ each are independently a monovalent branched hydrocarbon group having a hydrocarbon group at α- or β-position and having 3 to 10 carbon atoms or a monovalent cyclic hydrocarbon group having 3 to 10 carbon atoms, and $R^3$ is a tertiary hydrocarbon group having 4 to 10 carbon atoms.

* * * * *